(12) United States Patent
Koblasz et al.

(10) Patent No.: US 8,169,329 B2
(45) Date of Patent: May 1, 2012

(54) FLUID DETECTING MATTRESS COVER AND MONITORING SYSTEM

(76) Inventors: Arthur Koblasz, Atlanta, GA (US); Ronald Paul Crisman, Portland, OR (US)

(*) Notice: Subject to any disclaimer, the term of this patent is extended or adjusted under 35 U.S.C. 154(b) by 430 days.

(21) Appl. No.: 12/532,354

(22) PCT Filed: Mar. 19, 2008

(86) PCT No.: PCT/US2008/057498
§ 371 (c)(1), (2), (4) Date: Sep. 21, 2009

(87) PCT Pub. No.: WO2008/115987
PCT Pub. Date: Sep. 25, 2008

(65) Prior Publication Data
US 2010/0109684 A1    May 6, 2010

Related U.S. Application Data

(60) Provisional application No. 60/918,779, filed on Mar. 19, 2007.

(51) Int. Cl.
*G08B 23/00* (2006.01)

(52) U.S. Cl. .................. 340/573.5; 340/602; 340/636.15

(58) Field of Classification Search ............... 340/573.5, 340/573.6, 573.7, 602, 593–594, 636.11–636.13, 340/636.15, 660, 662
See application file for complete search history.

(56) References Cited

U.S. PATENT DOCUMENTS

| | | | | |
|---|---|---|---|---|
| 4,474,185 A * | 10/1984 | Diamond | ...................... | 600/535 |
| 5,664,273 A * | 9/1997 | Obriot | ............................... | 5/724 |
| 6,647,574 B2 * | 11/2003 | Weber | ............................... | 5/719 |
| 6,719,708 B1 * | 4/2004 | Jansen | ........................... | 600/587 |
| 7,076,822 B2 * | 7/2006 | Pearce | ........................... | 5/655.5 |

* cited by examiner

*Primary Examiner* — Daniel Previl
(74) *Attorney, Agent, or Firm* — Gardner Groff Greenwald & Villanueva, PC

(57) ABSTRACT

Apparatus, systems, and methods are described for detecting moisture on a mattress cover. Conductive leads affixed to the mattress cover are configured in loop patterns, and adjacent conductive loops are positioned equidistant to one another to provide equal sensitivity to moisture at any location on the mattress cover. A quick-release connector allows the conductive leads to be quickly connected to an electrical monitoring circuit. The continuity of each conductive lead is periodically checked using a test signal. Moisture is detected by applying a different voltage level to adjacent conductive leads and measuring the current flowing between the leads. When moisture or a broken conductive lead is detected, an alarm signal is communicated to an attendant. The alarm signal is repeated at periodic intervals until the electrical monitoring circuit detects that the alarm condition has been corrected. The attendant's response time is recorded for future performance evaluations.

20 Claims, 7 Drawing Sheets

FLUID DETECTING MATTRESS COVER AND MONITORING SYSTEM

CROSS-REFERENCE TO RELATED APPLICATIONS

This patent application claims priority to U.S. provisional application having Ser. No. 60/918,779, entitled "Improved Fluid Detecting Mattress Cover and Monitoring System," filed Mar. 19, 2007 which is hereby incorporated herein by reference in its entirety.

BACKGROUND

Patients lying on wet sheets for prolonged periods are more likely to develop decubitus ulcers (pressure sores) and/or nosocomial infections (hospital acquired infections). Both of these pathologies are reported as leading causes of accidental death in healthcare facilities and are identified by some government organizations and insurance companies as preventable medical errors.

Hospital mattresses form a platform for delivering acute and long-term care to patients. In recent years, increasing attention has been paid to mattress specifications, including their ability to comfortably support a recumbent or semi-recumbent patient, prevent pressure sores, stabilize patients after surgery, reduce the risk of rolling off the mattress, and facilitate nursing management of the patient during toileting and sponge bathing. The mattress surfaces are constructed to be impenetrable to body fluids so that the mattress inner core, which is normally comprised of foam materials, does not become contaminated.

To avoid spreading an infection to the next patient lying on the mattress, hospitals typically wipe the mattress surface with a cloth soaked in an antiseptic solution. The antiseptic solution is formulated to kill infectious organisms, but the recommended cleaning procedure requires the mattress to air-dry between patients. In some instances, the next patient arrives before the air-drying has been completed. Transport beds are particularly susceptible to this problem since patients are sometimes exposed to mattresses that are never cleaned between patient uses.

Wiping a mattress surface with an antiseptic cloth can leave a residue of dried human exudates or excrements on the mattress surface. The next wet sheet can create a pathway for infectious organisms to reach the mattress surface. If the mattress is coated with years of exudates and excrements from prior patients, the infectious organisms will be more likely to proliferate and infect the patient via open wounds or catheters. Some patients remain exposed to wet sheets for long periods of time, which increases their probability of acquiring infections or pressure sores. Caregivers are expected to check on their assigned patients to minimize each patient's exposure time to body fluids, but increased demands imposed on caregivers sometimes makes this monitoring task very difficult. Too often, patients remain exposed to body fluids for longer periods of time than the expected standard of care.

Each year, many patients experience increased hospital stays, poor health outcomes, or die, as a result of nosocomial infections. The prevalence of antibiotic resistant microorganisms, such as S. aureus and C. difficile, is increasing dramatically in both clinical and homecare settings making the current mattress cleaning methods ineffective and hazardous. Pressure sores develop from complex mechanical, micro vascular and pathological conditions interacting to cause histological breakdown of the skin. Exposure to body fluids increases the probability of both pressure sores and infections in a time-dependent fashion. Serious problems arise when attendants are unable or unwilling to frequently check on their patients.

Body fluids are electrolytic solutions that can be detected using conductive leads immersed in the body fluids. However, a major problem occurs when a conductive lead becomes fractured or when a connector device is improperly connected. The fractured lead or inoperative connector does not allow detection of the body fluid and thus provides a false negative indication. This equipment failure increases the time that the patient is exposed to body fluids, which is precisely what the electronic monitoring is supposed to prevent.

SUMMARY

It should be appreciated that this Summary is provided to introduce a selection of concepts in a simplified form that are further described below in the Detailed Description. This Summary is not intended to be used to limit the scope of the claimed subject matter.

Apparatus, systems, and methods described herein provide for the monitoring and detection of moisture within or on the surface of a mattress cover. According to one aspect of the disclosure provided herein, a fluid-detecting mattress cover includes a number of attached conductive loops. Each conductive loop includes a conductive lead with two terminal endings attached to a connector. The connector may be electrically connected to a monitoring circuit that can detect a variance in an electrical signal applied to the connector. The conductive loops are positioned in a region of the mattress cover in a manner that places them approximately equidistant from one another. Doing so ensures that the sensitivity of the conductive loops to moisture will be uniform throughout that region of the mattress cover.

According to another aspect described herein, a voltage is applied to a conductive loop. The conductive loop is attached to a region of a mattress cover equidistant from a second conductive loop attached to the mattress cover. Another voltage is applied to the second conductive loop and the electrical current between the two loops is monitored. When the current between the conductive loops satisfies a threshold alarm characteristic, an alarm is activated to alert someone of the presence of moisture on the mattress cover.

According to yet another aspect of the disclosure provided herein, a mattress cover fluid-detection system includes a mattress cover and a signal analysis system. The mattress cover is sized to cover the entire top surface of a mattress and has conductive loops positioned approximately equidistant from one another in a manner that provides for uniform moisture sensitivity across the region of the mattress cover to which the conductive loops are attached. The conductive loops each have a conductive lead with two terminal endings attached to a single connector. The connector is configured to attach to an electrical monitoring circuit that can detect a variance in an electrical signal applied to the conductive loops. When a threshold variance is detected, an alarm is activated.

The features, functions, and advantages that have been discussed can be achieved independently in various embodiments of the present invention or may be combined in yet other embodiments, further details of which can be seen with reference to the following description and drawings.

BRIEF DESCRIPTION OF THE DRAWINGS

Other embodiments of the invention can be seen with reference to the following description and drawings.

DETAILED DESCRIPTION

Figure 1A:
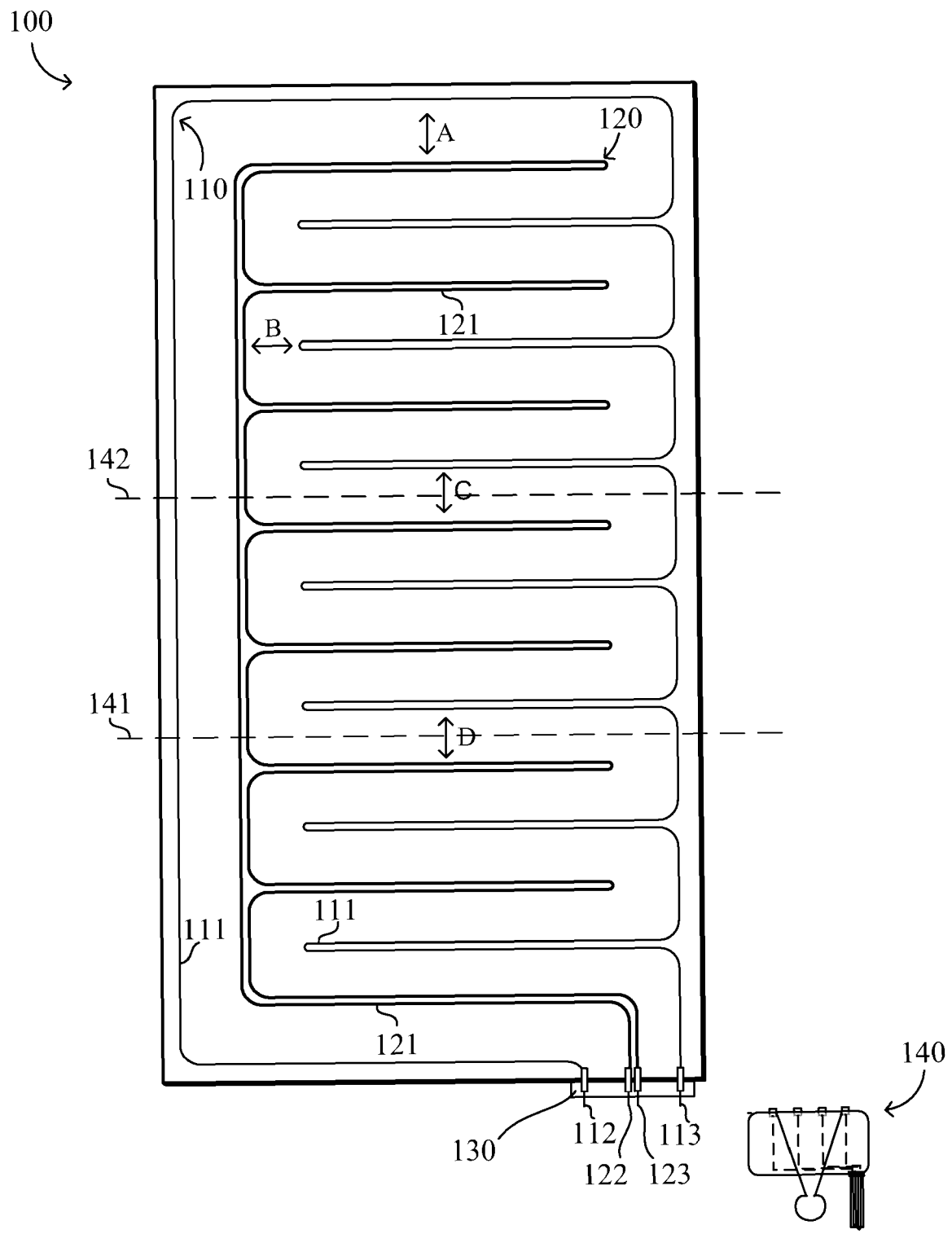
FIG. 1A is a top view of a mattress cover showing a configuration of the conductive leads forming continuous loop patterns for detecting fluid on the mattress cover and allowing the continuity of each conductive lead to be checked periodically according to various embodiments presented herein.

The following detailed description is directed to apparatus, systems, and methods for detecting and monitoring moisture on the top surface of a mattress cover. References are made to the accompanying drawings that form a part hereof, and which are shown by way of illustration, specific embodiments, or examples. Referring now to the drawings, in which like numerals represent like elements through the several figures, moisture detection and monitoring will be described.

FIG. 1A shows a top view of a mattress cover 100 according to one embodiment of the disclosure provided herein. The mattress cover 100, in combination with an electrical monitoring circuit as described herein, detects moisture on the mattress cover surface using conductive loops 110 and 120 imbedded inside or affixed to the top surface of the mattress cover 100. The conductive loops 110 and 120 each include a conductive lead 111 and 121, respectively, that begins at a common connector 130, traverses the surface of the mattress cover 100, and terminates back at the common connector 130. Each end of each conductive lead 111 and 121 includes a terminal ending 112, 113, 122, or 123 at the common connector 130 for electrically connecting the conductive loops 110 and 120 to an electrical monitoring circuit that measures the conductance (or resistance) between the two conductive leads 111 and 121, as well as detects faults within a single conductive lead, as will be described below. For example, the conductive loop 110 includes the conductive lead 111 with terminal endings 112 and 113 at the common connector 130. Similarly, the conductive loop 120 includes the conductive lead 121 with terminal endings 122 and 123 at the common connector 130.

The common connector 130 is configured to electrically connect the terminal endings 112, 113, 122, and 123 to the electrical monitoring circuit via a quick-release connector 140. According to various embodiments, the terminal endings 112, 113, 122, and 123 may include but are not limited to, small gauge electrical wire, conductive thread, conductive fabric, metal foil, evaporated metal, electroplated metal, conductive ink, or conductive paint. Similarly, the conductive leads 111 and 121 may include, but are not limited to, small gauge electrical wire, conductive thread, conductive fabric, metal foil, evaporated metal, electroplated metal, conductive ink, or conductive paint. The conductive leads 111 and 121 can be affixed to the top surface of a single waterproof layer or positioned between an absorbent, protective top layer and a waterproof bottom layer, as described further below.

The two separate conductive loops 110 and 120 extend over the mattress cover surface while maintaining a constant spacing between the two loops as indicated by arrows A and B. This feature provides a more uniform sensitivity to moisture over the surface of the mattress cover, i.e. the same volume of fluid introduced at different locations on the surface will be detected with the same latency. An exception to the uniform spacing may occur as indicated by spacings C and D, near the axes of rotation of the mattress 141, 142 where the mattress is deformed to raise the back and knees of the patient.

Figure 1B:
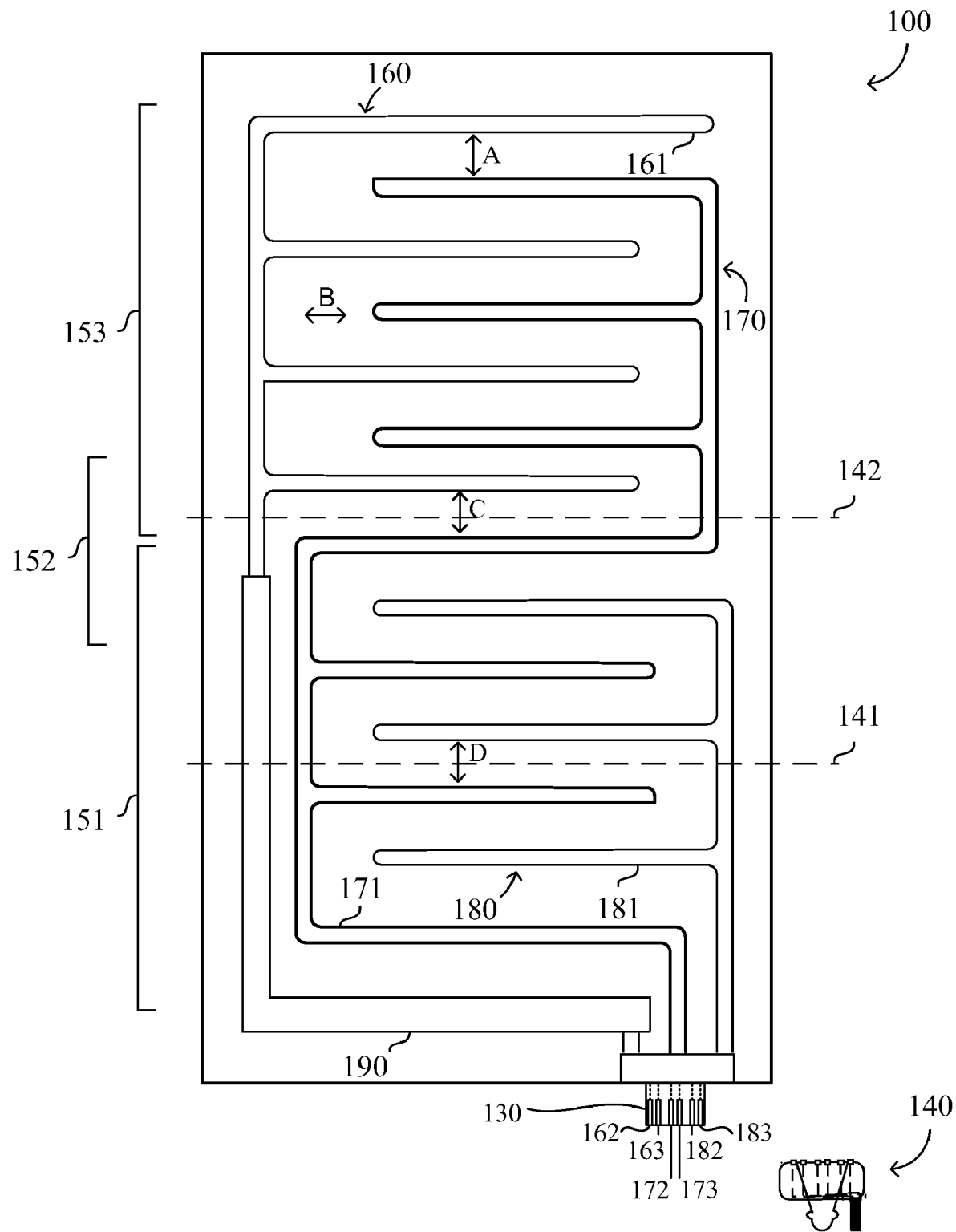
FIG. 1B is a top view of a mattress cover showing a configuration of conductive loops in three separate regions of the mattress cover surface for detecting fluid on the mattress cover in each of the three regions and allowing the continuity of each conductive lead to be checked, according to various embodiments presented herein.

FIG. 1B shows an alternative embodiment of the disclosure presented herein in which a mattress cover 100 includes three conductive loops 160, 170, and 180. Conductive loop 160 includes conductive lead 161 and terminal endings 162 and 163, and spreads across the upper-most region 153 defined by the rotational axis 142 of the mattress. Conductive loop 170 includes conductive lead 171 and terminal endings 172 and 173, and covers both regions 151 and 153. Conductive loop 180 includes conductive lead 181 and terminal endings 182 and 183, and covers the lowest region 151. The conductive loops 170 and 180 are together functional to detect fluid in the lowest region 151 of the mattress. The conductive loops 160 and 170 are together functional to detect fluid in the upper-most region 153. Fluid in the middle region 152 is identified when fluid is detected by conductive loops 170 and 180 and simultaneously by conductive loops 160 and 170.

It should be appreciated that the mattress cover 100 may include insulation 190 for insulating a lower portion of the conductive lead 161 of the conductive loop 160 where it traverses the lowest region 151 of the mattress cover 100. Insulating the conductive lead 161 in region 151 prevents an erroneous detection of fluid in region 153, when in fact the fluid is located in region 151. The terminal endings 162, 163, 172, 173, 182, and 183 are grouped together at a common connector 130, which provides an attachment receptacle for a connecting device such as quick-release connector 140. By utilizing the three-loop design shown in FIG. 1B, moisture can be detected and reported for each of the three separate regions of the mattress surface. For example, a higher priority alarm signal could be sent to an attendant when moisture is detected in the upper region of the mattress cover following neck surgery.

Figure 2A:
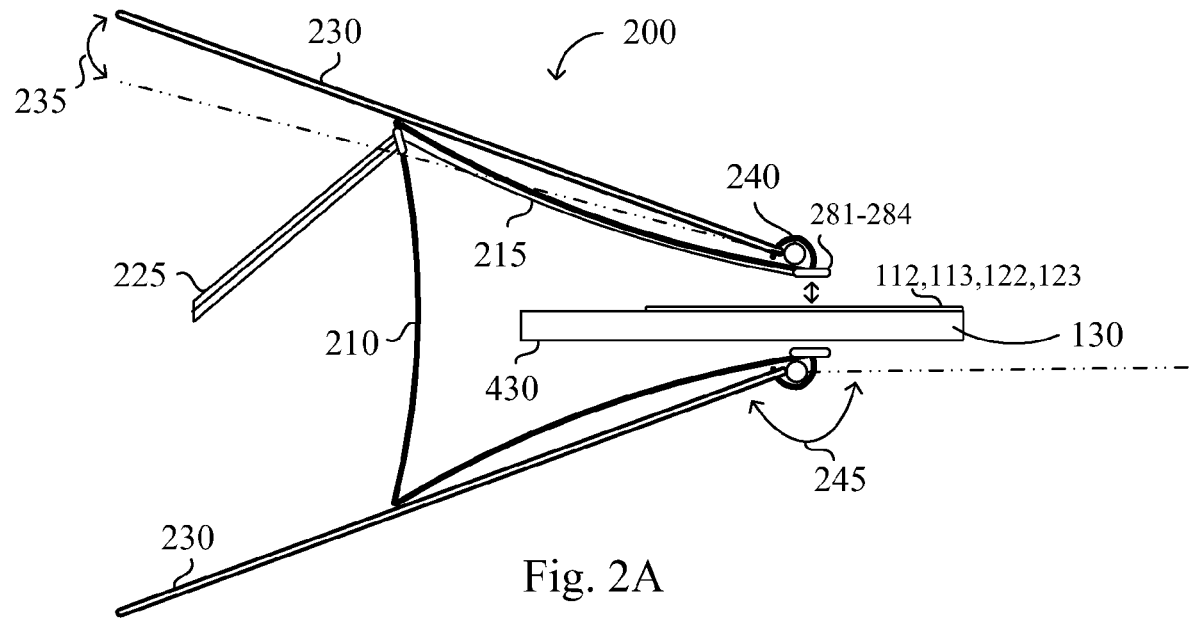
FIG. 2A is a side view of a clip type connector showing its construction elements and attachment to the mattress cover leads, according to various embodiments presented herein.

FIG. 2A is a side view of a quick-release connector 140, which is configured as a clamp-type connector 200. This clamp-type connector 200 consists of a leaf spring 210 that produces sustained compressive forces acting on conductive pads 281, 282, 283, and 284, shown in FIG. 2B. Electrical wires 215 connect the conductive pads 281, 282, 283, and 284 to a ribbon cable 225, which is connected to the electrical monitoring circuit. To open the jaws 240 of the clamp-type connector 200, two lever arms 230 are pushed towards each other as indicated by arrow 235, compressing leaf spring 210 while opening the jaws 240 of the clamp. The compressing leaf spring 210 biases the clamp-type connector 200 to return to a closed position. Releasing the two lever arms 230 allows both arms to rotate as indicated by arrow 245, closing on the common connector 130 shown in FIG. 1A such that the conductive pads 281, 282, 283, and 284 contact the terminal endings 112, 122, 123, and 113, respectively, of the common connector 130.

Figure 2B:
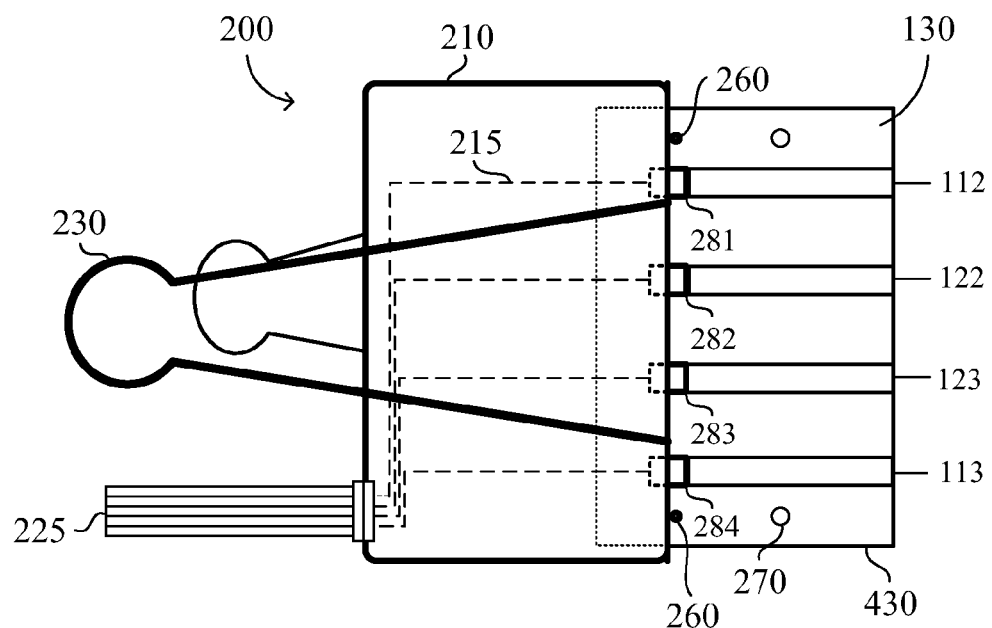
FIG. 2B is a top view of a clip type connector showing its construction elements and attachment to the mattress cover leads, according to various embodiments presented herein.

In FIG. 2B, the common connector 130 of the mattress cover 100 shown in FIG. 1 is positioned inside the jaws 240 of a clamp-type connector 200. Guide pegs 260 located on each side of clamp-type connector 200 maintain a proper alignment with respect to the common connector 130 by holding the two guide pegs 260 inside two guide holes 270. This assures alignment of the conductive pads 281, 282, 283, and 284 with respect to the terminal endings 112, 122, 123, and 113. It should be appreciated that the guide holes 270 can be reinforced by metal eyelets, by buttonhole stitching, or by any other reinforcing material.

Figure 3A:
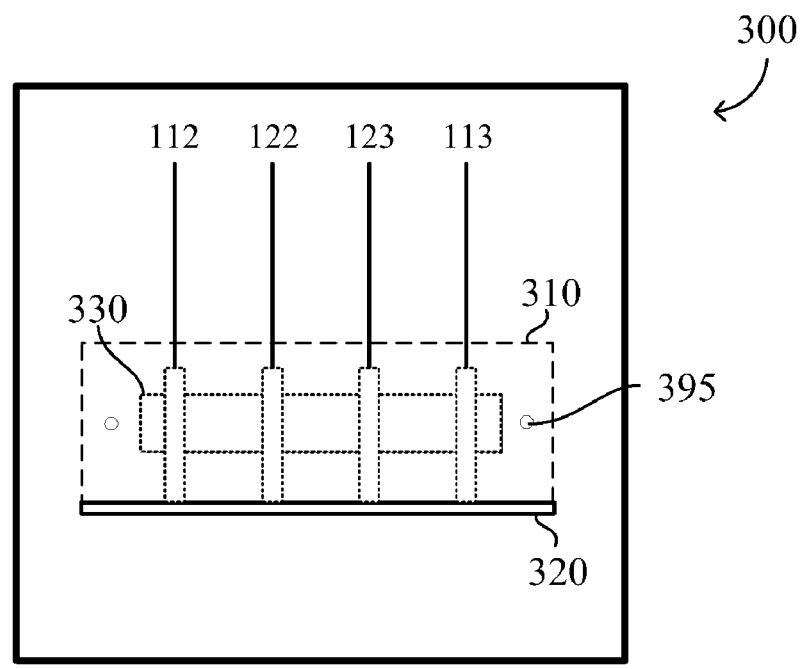
FIG. 3A is a top view of a magnetic type receptacle showing four terminal endings of a mattress cover containing two conductive loops, according to various embodiments presented herein.
Figure 3B:
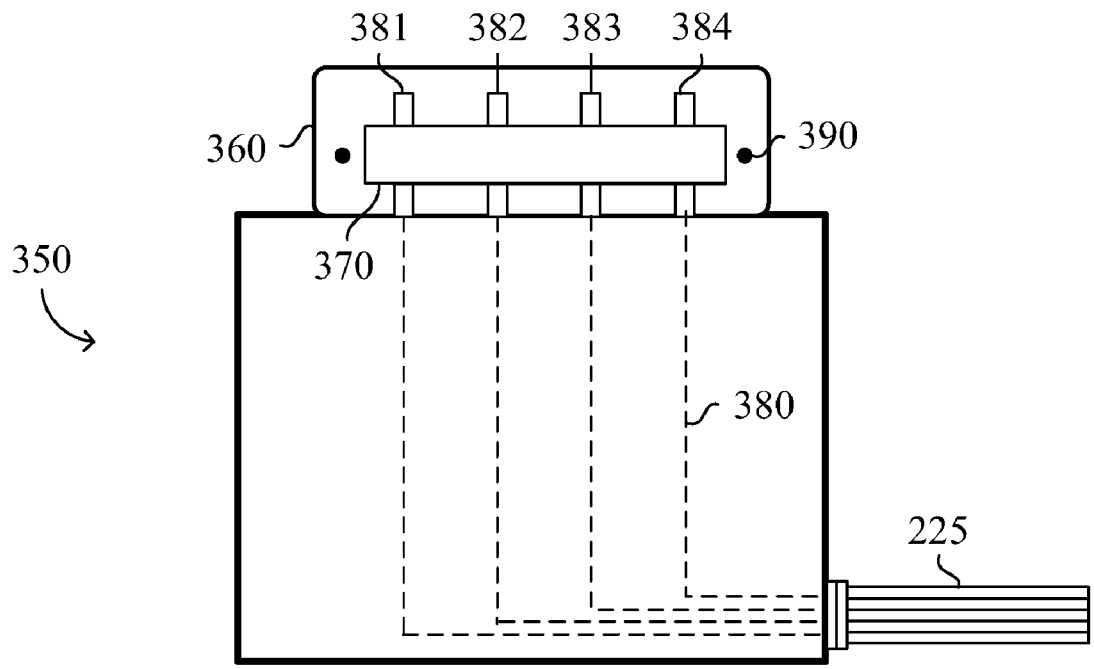
FIG. 3B is a top view of a magnetic type connector showing its construction elements for attachment to the mattress cover terminal endings in FIG. 3A, according to various embodiments presented herein.

FIG. 3A shows a common connector 130 configured as a magnetic-type connection flap 300 of the mattress cover 100. It is designed to function as a receptacle for a quick-release connector 140, such as a magnetic-type connector 350 shown in FIG. 3B. A tightly fitting receiving pocket 310 of the magnetic-type connection flap 300 contains terminal endings 112, 122, 123, and 113 inside a receptacle opening 320. A pocket 330 containing a strip of ferromagnetic material, which is attracted to a magnet 370 inside the magnetic-type connector 350, thereby pressing the terminal endings 112, 122, 123, and 113 against the conductive pads 381, 382, 383, and 384, respectively. Small pegs 390 are positioned inside alignment holes 395. The conductive pads 381, 382, 383, and 384 are thus aligned properly and held firmly against the terminal endings 112, 122, 123, and 113 while allowing the magnetic-type connector 350 to be inadvertently pulled away from the mattress cover receptacle 300 without damaging the magnetic-type connection flap 300 or the magnetic-type connector 350. The conductive pads 381, 382, 383, and 384 are connected to a ribbon cable 225 via electrical leads 380 within the magnetic-type connector 350.

According to various embodiments, the mattress cover 100 is composed of different layers of materials that are selected to make the mattress cover either disposable or washable. Different designs are depicted in FIG. 4. Bacteriostatic additives can be applied to any of the mattress cover materials. As described above, the conductive leads 111 and 121 may be manufactured from one or more layers of metal foil, conductive fabric, conductive thread, conductive paint, conductive ink, an evaporative coating of metal, an electroplated metal, or any other suitable conductive material. For example, conductive threads can be stitched or woven into a top absorbent layer of fabric or paper. Alternatively, conductive ink can be applied to the top surface of the waterproof material, or the conductive loops can be created using PC Board fabrication methods.

In a disposable version of the mattress cover, the waterproof layer can be comprised of a thin and flexible waterproof material, e.g., biodegradable Polyethylene, Polystyrene, or Cellophane. Recyclable materials like TYVEK, Nylon or PET (polyethylene terephthalate) are equally desirable. The waterproof layer can be used as a durable substrate for a printed circuit, fabricated like a flexible PC Board. A thin layer of foam or polymer reinforced paper can be used for the top absorbent layer. The top absorbent layer protects the conductive leads from being scratched or fractured. The top layer also absorbs a small amount of sweat and breathes slightly. The middle layer is composed of conductive leads that not only detect moisture between the leads, but also help conduct heat away from any hot spots on the surface of the mattress cover.

In a washable version of the mattress cover, a soft, durable textile fabric can be used for the top absorbent layer, and a waterproof adhesive can be used to laminate the fabric to a waterproof backing material, being careful not to cover the surface of the conductive leads with the adhesive. Alternatively, a waterproof film can be sprayed onto the bottom surface of the fabric, again being careful not to completely cover the conductive leads. The conductive leads can be created by stitching or weaving conductive threads into the fabric.

Figure 4A:
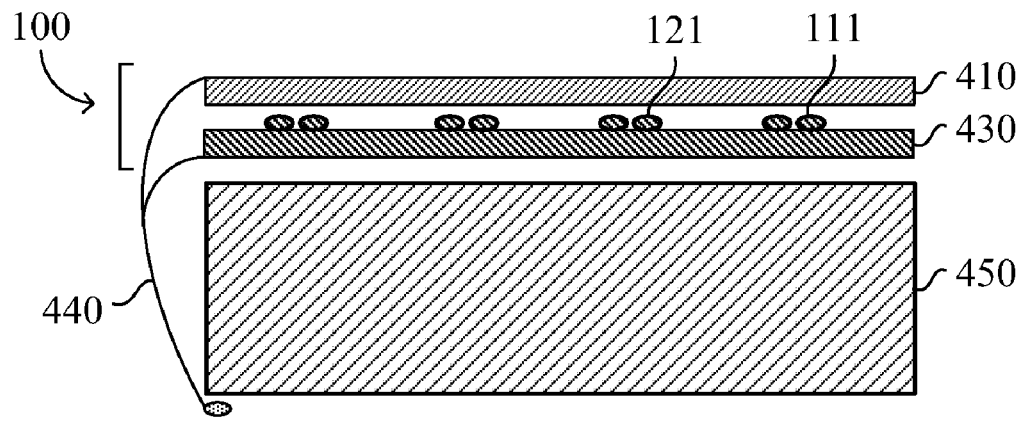
FIG. 4A is a cross-section of a mattress cover showing the arrangement of conductive leads between an absorbent top layer and a waterproof bottom layer, according to various embodiments presented herein.
Figure 4B:
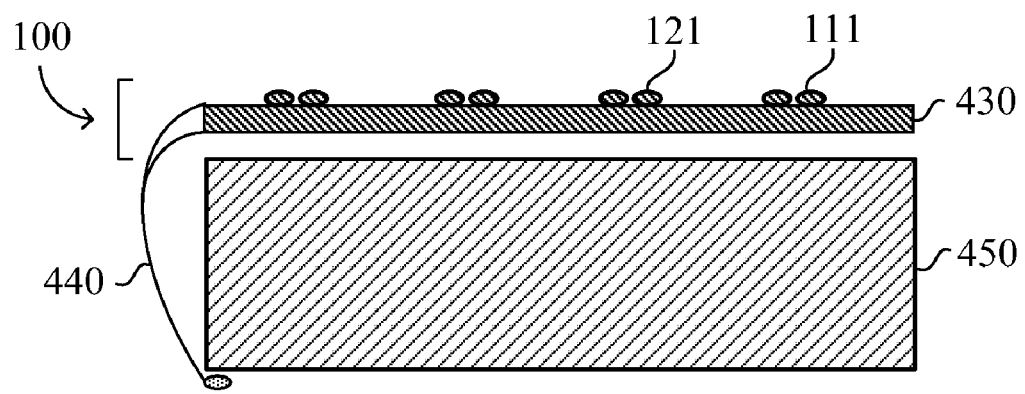
FIG. 4B is a cross-section of a mattress cover showing the arrangement of conductive leads affixed to a waterproof layer with no absorbent layer, according to various embodiments presented herein.
Figure 4C:
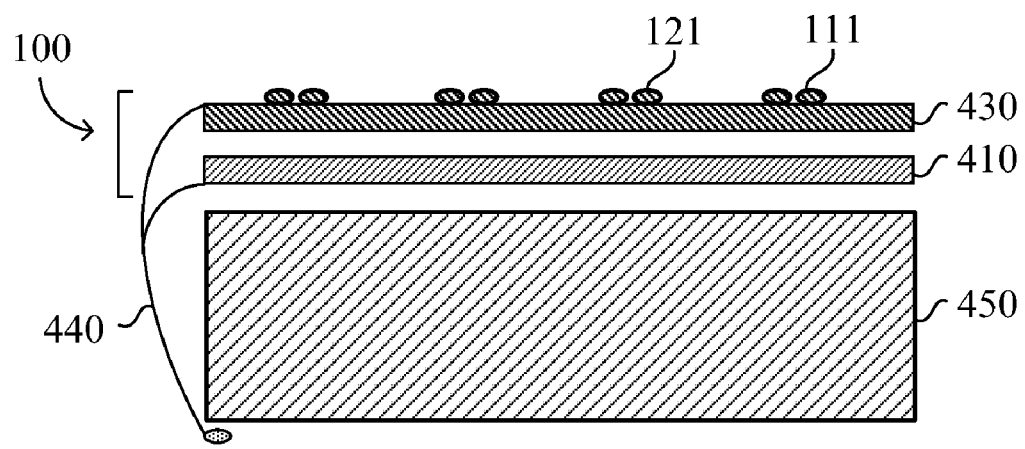
FIG. 4C is a cross-section of a disposable mattress cover showing the arrangement of conductive leads affixed to a waterproof top layer that is laminated to a reinforcing bottom layer, according to various embodiments presented herein.

FIG. 4A shows a cross-section of a mattress cover 100 with conductive leads 111 and 121 between an absorbent top layer 410 and a waterproof bottom layer 430. A fitted, elasticized skirt, strap, or other securing device 440 holds the mattress cover 100 securely in place over the mattress 450. In a cross-section presented in FIG. 4B, a mattress cover 100 has an arrangement of conductive leads 111 and 121 applied to a waterproof layer 430 with no absorbent layer 410. A fitted, elasticized skirt, strap, or other securing device 440 holds the mattress cover 100 securely in place over the mattress 450. FIG. 4C shows a cross-section of a mattress cover 100 with conductive leads 111 and 121 applied to a waterproof top layer 430. The waterproof layer 430 is laminated to a soft bottom layer 410. The soft bottom allows the mattress cover 100 to slide more easily across the surface of the mattress 450. It should be understood that the configurations shown throughout the figures are merely intended to be illustrative of the various embodiments described herein and are not intended to limit the disclosure to the configurations shown. For example, it should be appreciated that any number of conductive loops may be positioned at any location on the mattress cover 100. Additionally, any number of layers, washable or disposable, may be utilized within the mattress cover 100 without departing from the scope of this disclosure.

Figure 5:
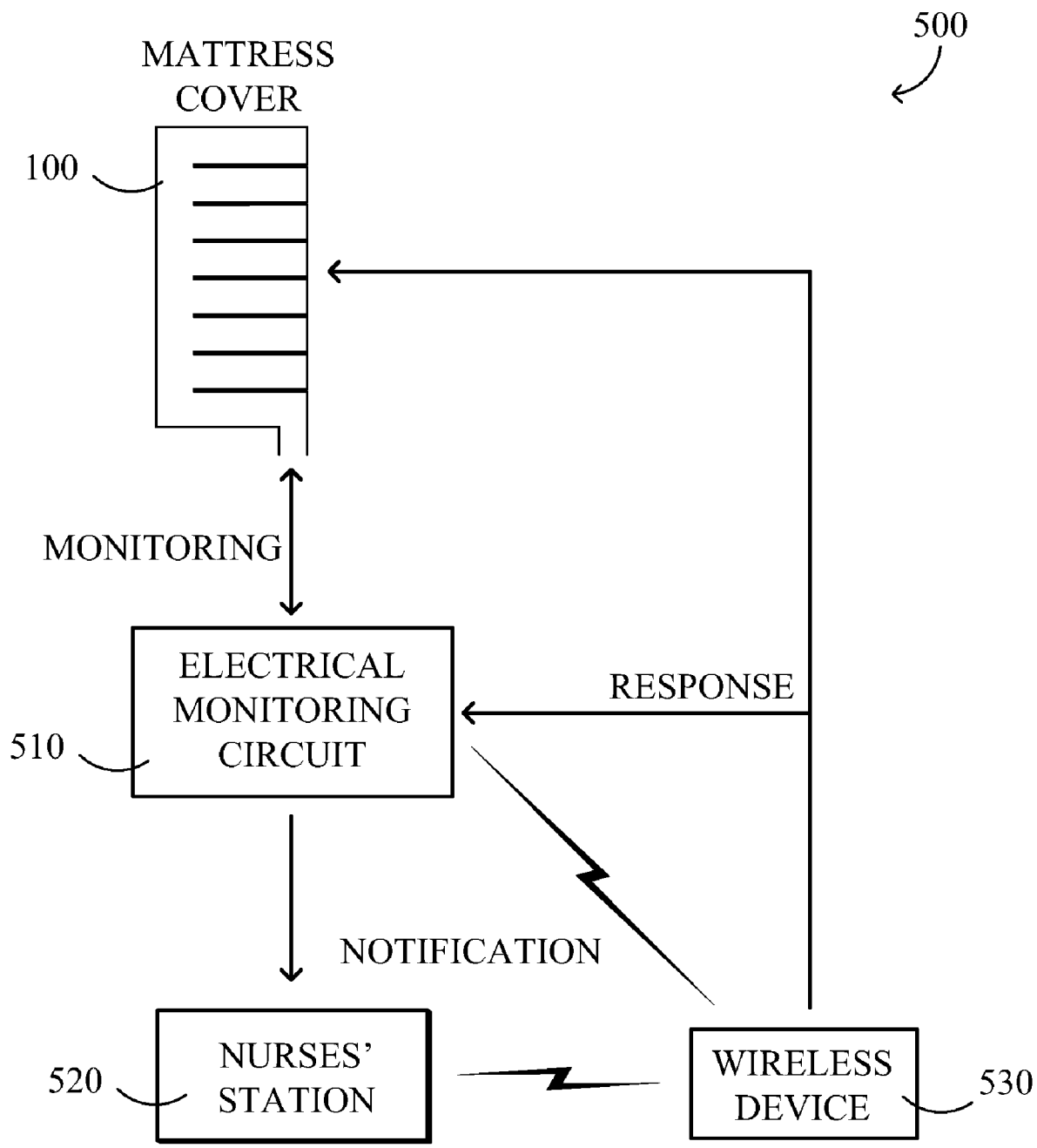
FIG. 5 is a block diagram depicting various components of a moisture detection and monitoring system according to various embodiments presented herein.

FIG. 5 shows a block diagram of a moisture detection and monitoring system 500 according to various embodiments described herein. The moisture detection and monitoring system includes the mattress cover 100, as described above, attached to an electrical monitoring circuit 510. The electrical monitoring circuit 510 is attached via a quick-release connector 140, such as the clamp-type connector 200 or the magnetic-type connector 350 to the terminal endings of the conductive leads in the mattress cover 100 via a common connector 140. The electrical monitoring circuit 510 identifies when a conductive lead or attached connector is malfunctioning. The electrical monitoring circuit 510 also monitors the electrical conductance between adjacent leads to detect when the mattress cover is coated with an electrolytic fluid.

The electrical monitoring circuit 510 can be located inside the mattress cover 100, inside the mattress 450, inside the footboard of the bed frame, inside or attached to the nightstand, or at any other location near the bed. The electrical monitoring circuit 510 monitors the integrity of each conductive loop 110 and 120, by periodically using an electrical signal, such as a known voltage or current signal, applied to one terminal ending of the loop and detecting whether the test signal arrives at the other terminal ending of the loop with no significant reduction in amplitude. This test of continuity also checks for a faulty quick-release connector 140.

The presence of fluid on the top surface of the mattress cover 100 between adjacent conductive loops 110 and 120 is detected by measuring the electrical conductance, resistance or other electrical signal variances between the adjacent conductive loops 110 and 120. For example, one of the conductive leads 111 can be charged with a positive voltage and the other conductive lead 121 can be charged with a negative voltage. If an electrolytic fluid (e.g. urine) is introduced onto the surface of the mattress cover, the charged ions in the fluid are attracted or repelled away from each conductive lead, depending on the +/− charge of the ion and the +/− charge of the lead. An accumulation of ions will occur at the surface of each conductive lead where electrons are exchanged between the ions and the metal atoms at the surface of the conductive lead. The accumulation of ions at each conductive lead surface is called "polarization," and the accumulation of ions produces a barrier to other ions.

If the voltage level at each conductive lead oscillates with a biphasic (+/−) modulation (e.g. sine wave, square wave or triangular wave modulation), and if the time mean of the oscillating voltage signal is zero, then the layers of ions accumulating at each conductive lead surface will be more effectively dispersed, thereby reducing the polarization. Polarization can be also reduced by minimizing the electrical current passing between the two conductive leads 111 and 121 via current limiting components in the electrical monitoring circuit 510, e.g. high-input impedance amplifiers or current limiting resistors.

If a voltage difference is maintained between the two conductive leads 111 and 121, the quantity of charged ions in the fluid can be estimated by measuring the oscillating electrical current passing through the electrical monitoring circuit. A small accumulation of sweat on the mattress cover will produce a small level of oscillating current passing between the two conductive leads, which will be ignored. The frequencies of the oscillating voltage signals will be selected to have therapeutic value.

According to various implementations, when the oscillating current level between the two conductive leads 111 and 121 exceeds a predetermined peak or average threshold level, the electrical monitoring circuit 510 will trigger a "wet sheet" alarm at a nurses' station 520, which could be then forwarded to an attendant's wireless communication device 530. Alternatively, the alarm may be sent directly to the wireless communication device 530 instead of, or in addition to, the nurses' station 520. It should be understood that any type of alarm signals could be used, including but not limited to, a blinking light outside the patient's room, a prerecorded loudspeaker announcement (e.g. "Code Yellow in Room 322B"), a text message on a monitor or other computing device, or any other visual or audible notification method.

If the electrical monitoring circuit 510 detects that any conductive lead has been fractured or the connector is not functioning properly, a different alarm signal can be triggered, e.g. a different message sent to the nurses' station 520 and attendant's wireless communication device 530. The various alarm signals or other notifications may be sustained or repeated at periodic intervals until the electronic monitoring circuit 510 detects that an attendant has responded to the alarm code. The attendant's response is detected when the mattress cover is no longer wet or when a malfunctioning lead becomes operable.

At the end of each shift, the mattress alarm data can be automatically displayed and/or printed on a supervisor's computer. The data can include the date/time when each wet sheet alarm code was transmitted, the date/time when the wet sheet sensors detected that the bottom sheet was finally changed, and the attendant's name or employee number who was assigned the task. In addition to the above-described short-term storage and reporting of attendant performance data, longer-term data can be recorded and analyzed to reveal correlations between hospital acquired infections, pressure sores and wet sheet exposures. It should be understood that the electrical monitoring circuit 510 may include a processor, as well as data storage, such as RAM, ROM, and/or mass storage devices or other computer storage media capable of storing system data and computer executable instructions for performing the various detection, monitoring, and notification processes described herein.

Figure 6:
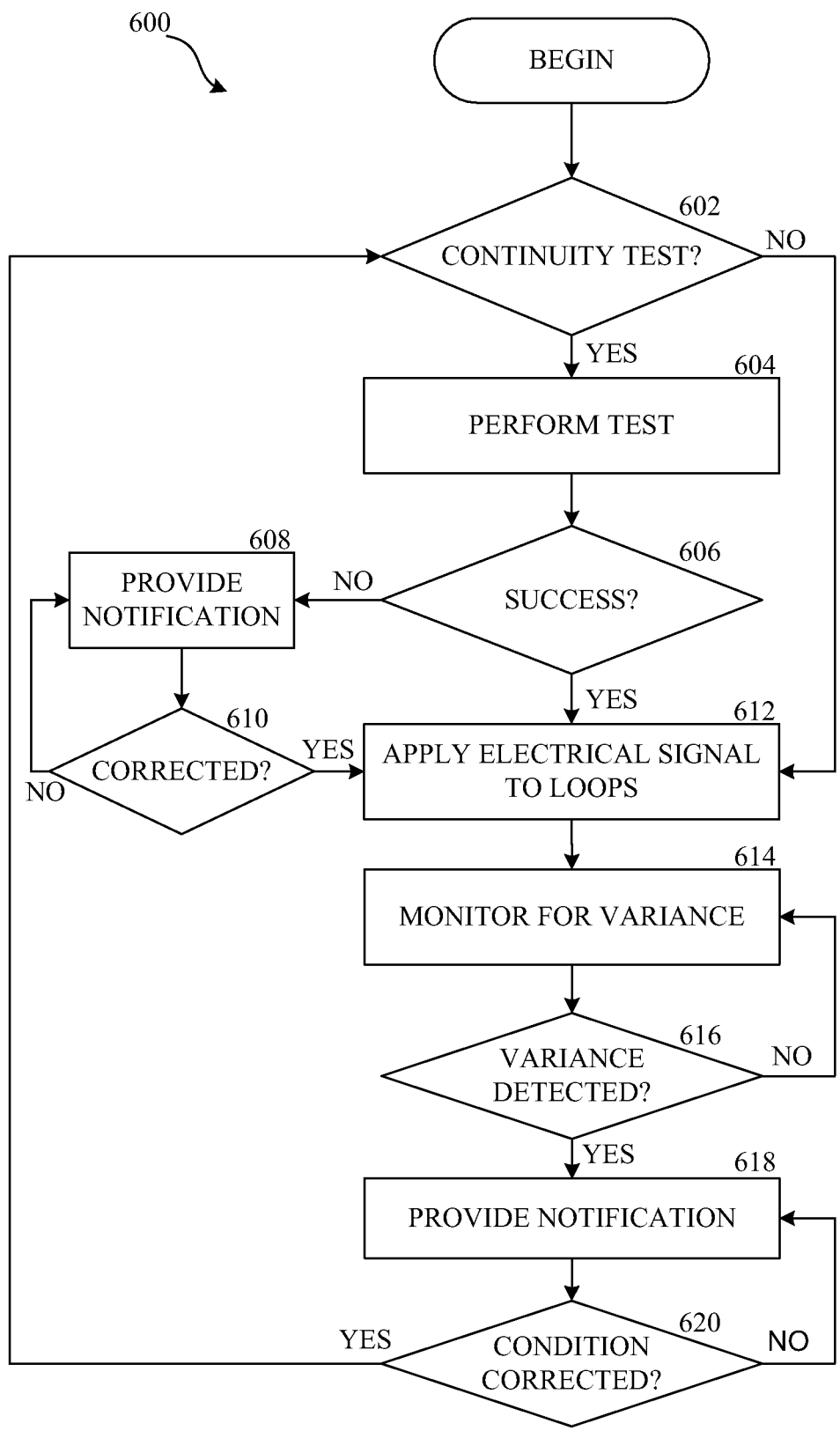
FIG. 6 is a flow diagram illustrating a method for detecting and monitoring for moisture on a mattress cover according to various embodiments presented herein.

Turning now to FIG. 6, an illustrative routine 600 for detecting moisture associated with a mattress cover 100 will now be described in detail. It should be appreciated that more or fewer operations may be performed than shown in the FIG. 6 and described herein. Moreover, these operations may also be performed in a different order than those described herein. The routine 600 is performed by the electrical monitoring circuit 510. The routine 600 begins at operation 602, where a determination is made as to whether a continuity test of one or more of the conductive loops 110 and 120 should be performed. A request may be received from an attendant or may be pre-programmed to execute at periodic intervals. If a continuity test is not to be performed, the routine 600 proceeds to operation 612 and continues as described below.

However, if at operation 602, it is determined that a continuity test is to be performed, then the routine 602 continues to operation 604, where the test is performed. As described above, the continuity of a conductive loop may include applying an electrical signal to one of the terminal endings and measuring the signal at the other terminal ending to determine whether a significant signal loss or other variance has been detected. If so, a defect in the conductive loop being tested is likely. From operation 604, the routine 600 continues to operation 606 where a determination is made as to whether the test was successful, meaning whether or not a variance in the electrical signal was detected. If the test was successful, then the routine 600 continues to operation 612 and continues as described below.

However, if the test was not successful, then the routine 600 proceeds to operation 608, where a notification is provided to an attendant. As described above, this notification may include any number and type of alarms, provided to a nurses' station 520, a wireless communication device 530, or to any other location or device. From operation 608, the routine 600 proceeds to operation 610, where the electrical monitoring circuit determines whether the condition has been corrected. If it has not been corrected, the routine 600 returns to operation 608 and continues to provide notification, and/or provides additional notification, until the condition has been corrected. Once corrected, the routine 600 proceeds to operation 612, where an electrical signal is provided to adjacent conductive loops 110 and 120 for monitoring and detecting of fluids on the surface of the mattress cover 100.

From operation 612, the routine 600 continues to operation 614, where the electrical monitoring circuit 510 monitors the adjacent conductive loops 110 and 120 for any variance in the electrical signal caused by fluid that traverses the conductive loops 110 and 120. At operation 616, a determination is made as to whether a variance or threshold alarm characteristic has been detected. If not, then the routine 600 returns to operation 614 and continues to monitor the electrical signal. However, if a variance in the electrical signal is detected, then the routine 600 continues to operation 618, where notification such as an alarm signal is provided to the nurses station 520, wireless communication device 530, or other location and/or device.

The routine 600 continues from operation 618 to operation 620, where the electrical monitoring circuit determines if the condition has been corrected. If the condition has not been corrected, then the routine 600 returns to operation 618 and continues to provide the notification and/or provides an additional notification. When the condition is corrected, the routine 600 returns to operation 602 and repeats as described above.

The subject matter described above is provided by way of illustration only and should not be construed as limiting. Various modifications and changes may be made to the subject matter described herein without following the example embodiments and applications illustrated and described, and without departing from the true spirit and scope of the present invention, which is set forth in the following claims.

What is claimed is:

1. A fluid-detecting mattress cover, comprising:
   a plurality of conductive loops attached to the fluid-detecting mattress cover, each conductive loop comprising a conductive lead with two terminal endings at a common connector, the common connector configured to electrically connect the two terminal endings from each of the plurality of conductive loops to an electrical monitoring circuit operative to detect a variance in an electrical signal applied to the common connector,
   wherein the plurality of conductive loops are positioned substantially equidistant from one another across a region of the fluid-detecting mattress cover to provide for uniform moisture sensitivity throughout the region.

2. The fluid-detecting mattress cover of claim 1, wherein each conductive loop comprises metal foil, electrical wire, conductive fabric, conductive thread, conductive paint, conductive ink, an evaporative coating of metal, or an electroplated metal.

3. The fluid-detecting mattress cover of claim 1, wherein the plurality of conductive loops comprises two conductive loops, wherein a first conductive loop traverses a surface of the fluid-detecting mattress cover adjacent to a perimeter of the surface and extends repeatedly from the perimeter across a center of the surface and back to the perimeter, and wherein a second conductive loop traverses the surface between the first conductive loop.

4. The fluid-detecting mattress cover of claim 1, wherein the common connector is configured to position each of the terminal endings for electrical connection to the electrical monitoring circuit via a connector device electrically connected to the electrical monitoring circuit.

5. The fluid-detecting mattress cover of claim 4, wherein the connector device comprises a clamp type connector.

6. The fluid-detecting mattress cover of claim 4, wherein the connector device comprises a magnetic type connector.

7. The fluid-detecting mattress cover of claim 4, wherein the connector device is configured to pull away from the conductive lead terminal without damaging the mattress cover or the connector device.

8. The fluid-detecting mattress cover of claim 1, further comprising:
   a top layer; and
   a bottom layer,
   wherein the plurality of conductive loops are affixed to either the top layer or the bottom layer.

9. The fluid-detecting mattress cover of claim 8, wherein the top layer comprises an absorbent material and the bottom layer comprises a waterproof material, and wherein the plurality of conductive loops are positioned between the top layer and the bottom layer.

10. The fluid-detecting mattress cover of claim 8, wherein the top layer comprises a waterproof material and the bottom layer comprises a reinforcing material, and wherein the plurality of conductive loops are affixed to a top surface of the waterproof material.

11. The fluid-detecting mattress cover of claim 8, wherein the top layer comprises a foam or polymer reinforced paper and the bottom layer comprises a biodegradable waterproof material, wherein the plurality of conductive loops are positioned between the top layer and the bottom layer, and wherein the mattress cover is disposable.

12. The fluid-detecting mattress cover of claim 8, wherein the top layer comprises a textile fabric and the bottom layer comprises a waterproof material, wherein conductive threads are stitched or woven into the textile fabric, and wherein the mattress cover is washable.

13. The fluid-detecting mattress cover of claim 1, wherein the electrical monitoring circuit is operative to detect a defect in conductive lead continuity in each conductive loop, to detect moisture between adjacent conductive loops, to activate an alarm in response to detecting a defect in conductive lead continuity, and to activate a different alarm in response to detecting moisture between adjacent conductive loops.

14. A method for detecting moisture on a mattress cover, comprising:
   applying a first voltage signal to a first conductive loop affixed to a region of the mattress cover;
   applying a second voltage signal to a second conductive loop affixed to the mattress cover in a position equidistant from the first conductive loop;
   monitoring an electrical current flowing between the first conductive loop and the second conductive loop;
   determining that the electrical current flowing between the first conductive loop and the second conductive loop satisfies a threshold alarm characteristic; and
   in response to determining that the electrical current level satisfies the threshold alarm characteristic, activating an alarm.

15. The method of claim 14, further comprising
   applying a third voltage signal to a third conductive loop affixed to an alternative region of the mattress cover;
   monitoring an electrical current flowing between the third conductive loop and the first or second conductive loop;
   determining that the electrical current satisfies a threshold alarm characteristic; and in response to determining that the electrical current satisfies the threshold alarm characteristic, activating an alarm that indicates that the mattress cover is wet at the alternative region of the mattress cover.

16. The method of claim 14, further comprising
   applying a time-varying voltage to each conductive lead with a time mean value equal to zero such that polarization of the conductive lead is minimized.

17. The method of claim 14, further comprising:
   applying an electrical signal to one end of the first conductive loop;
   measuring the electrical signal at an opposite end of the first conductive loop;
   detecting a variance in the electrical signal received at the opposite end as compared with the electrical signal applied to the first conductive loop; and in response to detecting the variance in the electrical signal, activating an alarm to indicate a defect in the first conductive lead or in the connector.

18. The method of claim 14, further comprising:

sustaining or repeating each alarm until the electrical monitoring circuit detects that an alarm condition has been corrected.

19. The method of claim 14, further comprising:

measuring and storing a response time of an attendant in correcting a mattress alarm condition and providing a notification of the response time.

20. A mattress cover fluid-detection system, comprising:

a mattress cover sized to cover an entire top surface of a mattress and comprising a plurality of conductive loops, each conductive loop comprising a conductive lead with two terminal endings at a common connector, the common connector configured to electrically connect the two terminal endings from each of the plurality of conductive loops to an electrical monitoring circuit, and wherein the plurality of conductive loops are positioned substantially equidistant from one another across the mattress cover to provide for uniform moisture sensitivity throughout the mattress cover; and the electrical monitoring circuit configured to electrically connect to each terminal ending via the common connector and operative to detect a defect in continuity of each of the plurality of conductive loops, to detect a variance in an electrical signal across adjacent conductive loops, and to activate an alarm upon the detection of the defect in continuity or the variance in the electrical signal.

* * * * *